United States Patent [19]

Shenoy

[11] 4,006,135

[45] Feb. 1, 1977

[54] HYDROXYMETHYL BENZODIAZEPINE DERIVATIVES

[75] Inventor: Umakant Devdas Shenoy, London, England

[73] Assignee: DDSA Pharmaceuticals, London, England

[22] Filed: July 11, 1974

[21] Appl. No.: 487,479

Related U.S. Application Data

[63] Continuation-in-part of Ser. No. 480,917, June 19, 1974, abandoned.

[52] U.S. Cl. .................. 260/239 BD; 260/294.8 C; 260/294.9; 260/295 F; 260/296 B; 424/244; 424/263
[51] Int. Cl.$^2$ .............. C07D 243/20; C07D 401/04
[58] Field of Search ............................ 260/239 BD

[56] References Cited

UNITED STATES PATENTS 3,391,138  7/1968  Archer et al. .............. 260/239 BD
3,682,888  8/1972  Podesva et al. ............ 260/239.3 D
3,819,602  6/1972  Fryer et al. ................. 260/239.3 D

FOREIGN PATENTS OR APPLICATIONS 1,359,286  7/1974  United Kingdom ......... 260/239 BD

OTHER PUBLICATIONS

Greenblatt et al., Benzodiazepines in Clinical Practice, (Raven Press, N.Y., 1974) pp. 10–12, Rm 666.B42G7

Primary Examiner—Alton D. Rollins
Attorney, Agent, or Firm—Burgess, Dinklage & Sprung

[57] ABSTRACT

Novel 1-hydroxymethyl-2-(N-alkyl-N-hydroxymethyl-)amino-1H-1,4-benzodiazepines and their 4-oxides, and acid addition salts thereof. Also a process for their preparation from 2-alkyl-amino-3H-1,4-benzodiazepines and their 4-oxides.

7 Claims, No Drawings

HYDROXYMETHYL BENZODIAZEPINE DERIVATIVES

This is a continuation-in-part of copending application Ser. No. 480,917 filed June 19, 1974 to Umakant Devdas Shenoy, and now abandoned.

BACKGROUND OF THE INVENTION

This invention provides 1-hydroxymethyl benzodiazepine derivatives, methods for their preparation and therapeutic compositions containing them.

3H-1,4-benzodiazepine derivatives are known, many of which have a useful action on the central nervous system and are regularly administered as tranquillizers in the field of human therapy. 1H-1,4-benzodiazepine derivatives are however hitherto unknown.

SUMMARY OF THE INVENTION

It is an object of the invention to provide novel 1H-1,4-benzodiazepine derivatives useful in the fields of human and animal therapy and as intermediates in the synthesis of other valuable drugs.

According to the invention there are provided benzodiazepine derivatives of the general formula I

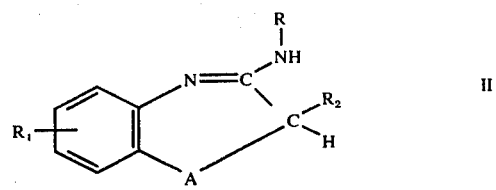

wherein $R_1$ represents a radical selected from the group consisting of hydrogen and halogen atoms and, trifluoromethyl, cyano, nitro, lower alkyl, lower alkoxy and lower alkylthio groups;

$R_2$ represents a radical selected from the group consisting of hydrogen atoms and hydroxy, lower alkyl, lower alkoxy and lower alkanoyloxy groups;

$R_3$ represents a radical selected from the group consisting of lower alkyl, hydroxy(lower alkyl), lower alkenyl and benzyl groups; and $R_4$ represents a radical selected from the group consisting of phenyl, (lower alkyl) phenyl, nitrophenyl, halophenyl and pyridyl groups;

4-oxides thereof and acid addition salts thereof and of the 4-oxides with therapeutically acceptable inorganic or organic acids.

The acid addition salts according to the invention may be with acids such as hydrochloric acid, hydrobromic acid, nitric acid, sulphuric acid, acetic acid, formic acid, phosphoric acid, perchloric acid, succinic acid, maleic acid, citric acid and fumaric acid.

As used herein the term 'halogen' means bromine, chlorine, fluorine or iodine. The term 'lower alkyl' refers to both straight-chain and branched-chain alkyl groups containing from 1 to 6 carbon atoms, for example methyl, ethyl, propyl, isopropyl, n-butyl, n-amyl and n-hexyl. The term 'lower alkenyl' means both straight-chain and branched-chain alkenyl groups containing from 2 to 6 carbon atoms, for example, vinyl allyl, butenyl, hexenyl, and isobutenyl. The term 'lower alkoxy' refers to both straight-chain and branched-chain alkoxy groups containing 1 to 6 carbon atoms, for example, methoxy, ethoxy and butoxy. The term 'lower alkanoyloxy' refers to both straight chain and branched chain alkanoyloxy groups containing from 2 to 6 carbon atoms, for example acetoxy, propionyloxy and butyryloxy.

Specifically the compounds of the present invention are useful for their psychotropic action on the central nervous system, for their tranquillizing, sedative and hypnotic properties. In such treatment they are generally employed in a dosage between 1 mg and 10 mg depending on the age and condition of the patient. In larger doses they produce sedation, and when the sedative dose is increased they have hypnotic effect. They can be applied in the form of a tablet, capsules, suppositories or syrup, or in injectable form. They can be formulated with adjuvants and excipients as is usual with products of this nature. This invention accordingly provides therapeutic compositions comprising one or more compounds according to this invention in admixture with a pharmacologically acceptable diluent or carrier.

This invention also provides a process for preparing the above compounds which comprises reacting, in acid conditions, a compound of the general formula II

wherein $R_1, R_2, R_3$, and A are as above defined, with formaldehyde. Certain suitable starting materials of the general formula II are described and claimed in British Pat. Specifications Nos. 864,824, 972,969, 986,903. The molar ration of the starting material of the general formula II to formaldehyde is preferably from 1:1 to 1:3.

The formaldehyde may be used in the form of formalin or may be generated in situ, for example by the action of acid on a solid polymer of formaldehyde, such as paraformaldehyde which has the formula $(CH_2O-)_n$ in which $n$ may be 100 or more, a polyoxymethylene which has the formula $HO(CH_2O-)_nH$ in which $n$ may be 100 or more, or S-trioxane represented by the formula $$O\text{-}CH_2\text{-}O\text{-}CH_2\text{-}O\text{-}CH_2$$

These solid polymers of formaldehyde are converted to formaldehyde by the acid in the reaction mixture.

The reaction is preferably carried out at room temperature (about 20° C) in solution in water, in an organic solvent for the starting benzodiazepine compound, for example an aliphatic alcohol containing from 1 to 3 carbon atoms, dioxan or tetrahydrofuran or in a mixture of water and such an organic solvent.

The reaction mixture should be acidic throughout the reaction. Suitable acids employed to maintain this acidity include hydrochloric acid, hydrobromic acid, nitric acid, sulphuric acid, acetic acid, formic acid, phosphoric acid, perchloric acid, succinic acid, maleic acid, fumaric acid and paratoluene sulphonic acid.

The starting material represented by the formula 11 can be used in the form of the free base or a suitable acid addition salt. Acid addition salts, for example hydrochloride salts, are preferable as they are easily soluble in water.

The product starts separating in about 5 to 10 minutes and separation is usually complete in about three days. The crude product obtained is usually in the form of an acid addition salt, the nature of which depends on the acidic component used in the reaction.

The following Examples illustrate this invention.

EXAMPLE 1

To a solution of 7-chloro-2-methylamino-5-phenyl-3H-1,4-benzodiazepine-4-oxide hydrochloride (33.6 g) in water (400 ml) in a 1 liter round-bottomed flask equipped with a magnetic stirrer was added concentrated hydrochloric acid (11 ml) and 40% formalin (20 ml). The flask was stoppered and stirred for 60 hrs. at room temperature (15° to 20° C). The precipitated solid was filtered, washed with water (2×25ml) and air dried. Crystallization from a mixture of methanol and ether yield 27 g 7-chloro-1-hydroxymethyl-2-(N-methyl-N-hydroxymethyl)amino-5-phenyl-1H-1,4-benzodiazepine-4-oxide hydrochloride.

M.P. 189°–190° C (with decomposition).

Analysis: for $C_{18}H_{19}Cl_2N_3O_3$. calculated: C: 54.55; H: 4.80; N: 10.60. found: C: 52.99; H: 4.78; N: 10.95.

EXAMPLE 2

To a solution of 7-chloro-2-methylamino-5-phenyl-3H-1,4-benzodiazepine-4-oxide (3 g) in 0.5 N hydrochloric acid (40 ml) in a 100 ml round-bottomed flask equipped with a magnetic stirrer was added 40% formalin (2 ml). The flask was stoppered and stirred for 60 hrs. at room temperature (15° to 20° C). The separated solid was filtered, washed with water (2×2.5 ml) and air dried. Crystallization from a mixture of methanol and ether yielded 2.4 g of 7-chloro-1-hydroxymethyl-2-(N-methyl-N-hydroxymethyl)amino-5-phenyl-1H-1,4-benzodiazepine-4-oxide hydrochloride. M.P. 189° to 190° C (with decomposition).

EXAMPLE 3

To a solution of 7-chloro-2-methylamino-5-phenyl-3H-1,4-benzodiazepine-4-oxide hydrochloride (13.44 g) in water (160 ml) in a 500 ml round-bottomed flask equipped with a magnetic stirrer was added concentrated HCl(4.4 ml) and paraformaldehyde (1.2 g). The flask was stoppered and stirred for 60 hrs. at room temperature (15° to 20° C). The separated product was filtered, washed with water (2×10 ml) and air dried. Crystallization from a mixture of methanol and ether yielded 5.0 g of 7-chloro-1-hydroxymethyl-2-(N-methyl-N-hydroxymethyl)amino-5-phenyl-1H-1,4-benzodiazepine-4-oxide hydrochloride. M.P. 189° to 190° C (with decomposition).

What I claim is:

1. A benzodiazepine derivative of the formula

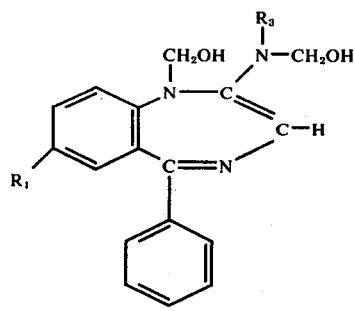

wherein
$R_1$ is a radical selected from the group consisting of hydrogen, halogen, trifluoromethyl, cyano, nitro, lower alkyl, lower alkoxy and lower alkylthio; and
$R_3$ represents a lower alkyl radical;
four oxides thereof and acid addition salts thereof and of the four oxides with therapeutically acceptable inorganic or organic acids.

2. 7-chloro-1-hydroxymethyl-2-(N-methyl-N-hydroxymethyl)amino-5-phenyl-1H-1,4-benzodiazepine-4-oxide hydrochloride.

3. A process for preparing a derivative of claim 1 which comprises reacting, in acid conditions, a compound of the formula

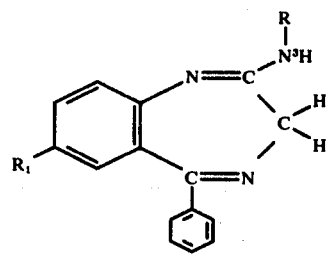

wherein
$R_1$ is hydrogen, halogen or a radical selected from the group consisting of trifluoromethyl, cyano, nitro, lower alkyl, lower alkoxy and lower alkylthio; and
$R_3$ is a lower alkyl radical, with formaldehyde.

4. A process according to claim 3 wherein the molar ratio of the benzodiazepine compound to formaldehyde is from 1:1 to 1:3.

5. A process according to claim 3, wherein the formaldehyde is generated in situ.

6. A process according to claim 3, carried out at room temperature in solution in a solvent selected from water, an organic solvent for the benzodiazepine compound, and a mixture of water and such an organic solvent.

7. A modification of a process according to claim 3, wherein the benzodiazepine compound is used in the form of an acid addition salt.

* * * * *

UNITED STATES PATENT AND TRADEMARK OFFICE
CERTIFICATE OF CORRECTION

PATENT NO. : 4,006,135
DATED : February 1, 1977
INVENTOR(S) : Umakant Devdas Shenoy It is certified that error appears in the above-identified patent and that said Letters Patent are hereby corrected as shown below:

Column 4, lines 20 and 21, "four oxides" should read -- 4-oxides --

Signed and Sealed this

Twenty-fourth Day of May 1977

[SEAL]

Attest:

RUTH C. MASON
Attesting Officer

C. MARSHALL DANN
Commissioner of Patents and Trademarks